US00PP10479P

United States Patent [19]

Zaiger et al.

[11] Patent Number: Plant 10,479

[45] Date of Patent: Jul. 7, 1998

[54] NECTARINE TREE 'ARCTIC BELLE'

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 40005 California Ave., all of Modesto, Calif. 95358

[21] Appl. No.: 845,193

[22] Filed: Apr. 21, 1997

[51] Int. Cl.[6] ..... A01H 5/00

[52] U.S. Cl. ..... Plt./40.1

[58] Field of Search ..... Plt./40.1

*Primary Examiner*—James R. Fryrer

[57] ABSTRACT

A new and distinct variety of nectarine tree (*Prunus persica* var. *nucipersica*); its novelty consists of the following unique combination of desirable features that are outstanding in a new variety:

1. Fruit with excellent flavor and eating quality.
2. Heavy and regular production of large size fruit.
3. Fruit with firm flesh, good handling and shipping quality.
4. Fruit with a high degree of attractive red skin color.
5. Fruit staying firm on the tree 8 to 10 days after maturity (shipping ripe).
6. Relatively uniform ripening of fruit throughout the tree.

1 Drawing Sheet

ORIGIN OF THE VARIETY

The present new variety of nectarine tree was developed by us in our experimental orchard located near Modesto, Calif., as an open pollinated seedling selection from a seedling with field identification number 141LB505. The seedling selection (141LB505) originated from an open pollinated Arctic Queen Nectarine (U.S. Plant Pat. No. 8,094) seed. A large number of these open pollinated seedlings were planted and grown under close observation by us, during which time one such seedling, which is of the present variety, having the especially desirable fruit characteristics described above, was selected for asexual propagation and commercialization.

SUMMARY OF THE VARIETY

The present new variety of nectarine tree is of large size, vigorous, upright growth and a productive and regular bearer of large, firm, white flesh semi-freestone fruit with good handling and shipping quality. The fruit is further characterized by having a mild, sub-acid, sweet taste with excellent flavor and eating quality; being relatively uniform in ripening throughout the tree and, in comparison to Arctic Rose Nectarine (U.S. Plant Pat. No. 7,889), the new variety has greater production of larger size fruit and is 4 to 5 days later in maturity.

DESCRIPTION OF THE PHOTOGRAPH

The accompanying color photographic illustration shows typical specimens of the foliage and fruit of the present new variety. The upper and lower surface of the leaves are shown along with the exterior and sectional view of the fruit divided in the suture plane to show flesh coloration, pit cavity and a stone remaining in place. The photograph was taken shortly after being picked at maturity (firm ripe) and the colors are as nearly true as reasonably possible in a color representation of this type.

DESCRIPTION OF THE VARIETY

The following is a detailed botanical description of the present new variety of nectarine tree, its flowers, foliage and fruit, based on observations of specimens grown in our experimental orchard located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Productivity.*—Productive.
- *Bearing.*—Regular.

Trunk:
- *Size.*—Medium stocky.
- *Texture.*—Medium shaggy.
- *Color.*—Brown to grayish brown (5-D-4) to (5-E-4).

Branches:
- *Size.*—Medium.
- *Surface.*—Smooth to medium rough.
- *Lenticels.*—Medium number. Medium size.
- *Color.*—Light brown to brown (6-D-4) to (6-E-4). Varies with age of growth.

Leaves:
- *Size.*—Average length — 5". Average width — 1½".
- *Form.*—Lanceolate, pointed.
- *Thickness.*—Medium.
- *Margin.*—Crenate.
- *Petiole.*—Medium length. Medium thickness.
- *Texture.*—Smooth.
- *Glands.*—Reniform. Number varies from 1 to 3. Average number 2. Medium size. Positioned primarily on base of leaf blade, few on upper portion of petiole.
- *Color.*—Upper surface — green to dark green (28-F-5) to (28-F-6). Lower surface — light green to green (28-F-6) to (28-E-7).

Flower buds:
- *Size.*—Medium to large.
- *Form.*—Plump.
- *Length.*—Medium.

Flowers:
- *Blooming period.—Date of first bloom:* Mar. 3, 1996. *Date of last bloom:* Mar. 7, 1996. Varies slightly due to climatic conditions.
- *Size.*—Large, showy.
- *Pollen.*—Present, self-fertile.
- *Color.*—Pink.

Fruit:
- *Maturity when described.*—Firm ripe.
- *Date of first picking.*—Jul. 5, 1996.
- *Date of last picking.*—Jul.12, 1996.
- *Size.*—Large. Average diameter axially 2⅞". Average transversely in suture plane 2⅞".

*Form.*—Nearly globose, slightly flattened at stem end, some fruit slightly larger in suture plane.
*Suture.*—Shallow, extends from base to apex.
*Ventral surface.*—Nearly rounded, some fruit slightly lipped.
*Apex.*—Usually rounded, varies from round to small apical point.
*Base.*—Retuse.
*Cavity.*—Rounded, slightly elongated in suture plane. Average depth — ⅜". Average breadth — ⅝".

Flesh:
*Ripens.*—Evenly.
*Texture.*—Firm.
*Juice.*—Moderate.
*Aroma.*—Slight.
*Fibers.*—Moderate amount, medium size, tender.
*Flavor.*—Excellent, mild, sub-acid, sweet.
*Eating quality.*—Excellent.
*Color.*—White to pinkish white (7-A-1) to (7-A-3). Pit cavity — pale red to pastel red (10-A-7) to (10-B-7). Slight bleeding of red (10-A-5) into flesh around pit cavity, heavier near apex.

Skin:
*Thickness.*—Medium.
*Texture.*—Medium, tenacious to the flesh.
*Tendency to crack.*—None.
*Down.*—Wanting.
*Color.*—White to yellowish white ground color (5-A-1) to (5-A-4). Nearly overspread with red to orient red (10-C-6) to (10-C-8). Speckled pattern of small areas of ground color showing, randomly spaced.

Stone:
*Type.*—Semi-freestone. Small areas of fibers and flesh adhere to the stone.
*Size.*—Large. Average length — 1⅛". Average breadth — 1⅛". Average thickness — ¾".
*Form.*—Obovate.
*Base.*—Usually straight. Varies from straight to rounded.
*Apex.*—Acuminate.
*Sides.*—Equal to unequal.
*Surface.*—Irregularly furrowed toward apex, pitted toward base, pit cavities vary from round to elongated.
*Ridges.*—Rounded.
*Tendency to split.*—None.
*Color.*—Brown to reddish brown (9-D-4) to (9-D-8).

Use: Dessert.
*Market.*—Local and long distance.

Keeping quality: Good.
Shipping quality: Good.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth, and a productive and regular bearer of large size, white flesh, semi-freestone fruit with excellent flavor and eating quality; the fruit is further characterized by having firm flesh, good handling and shipping quality and, in comparison to the white flesh Arctic Rose Nectarine (U.S. Plant Pat. No. 7,889), the new variety has greater production of larger size fruit and is 4 to 5 days later in maturity.

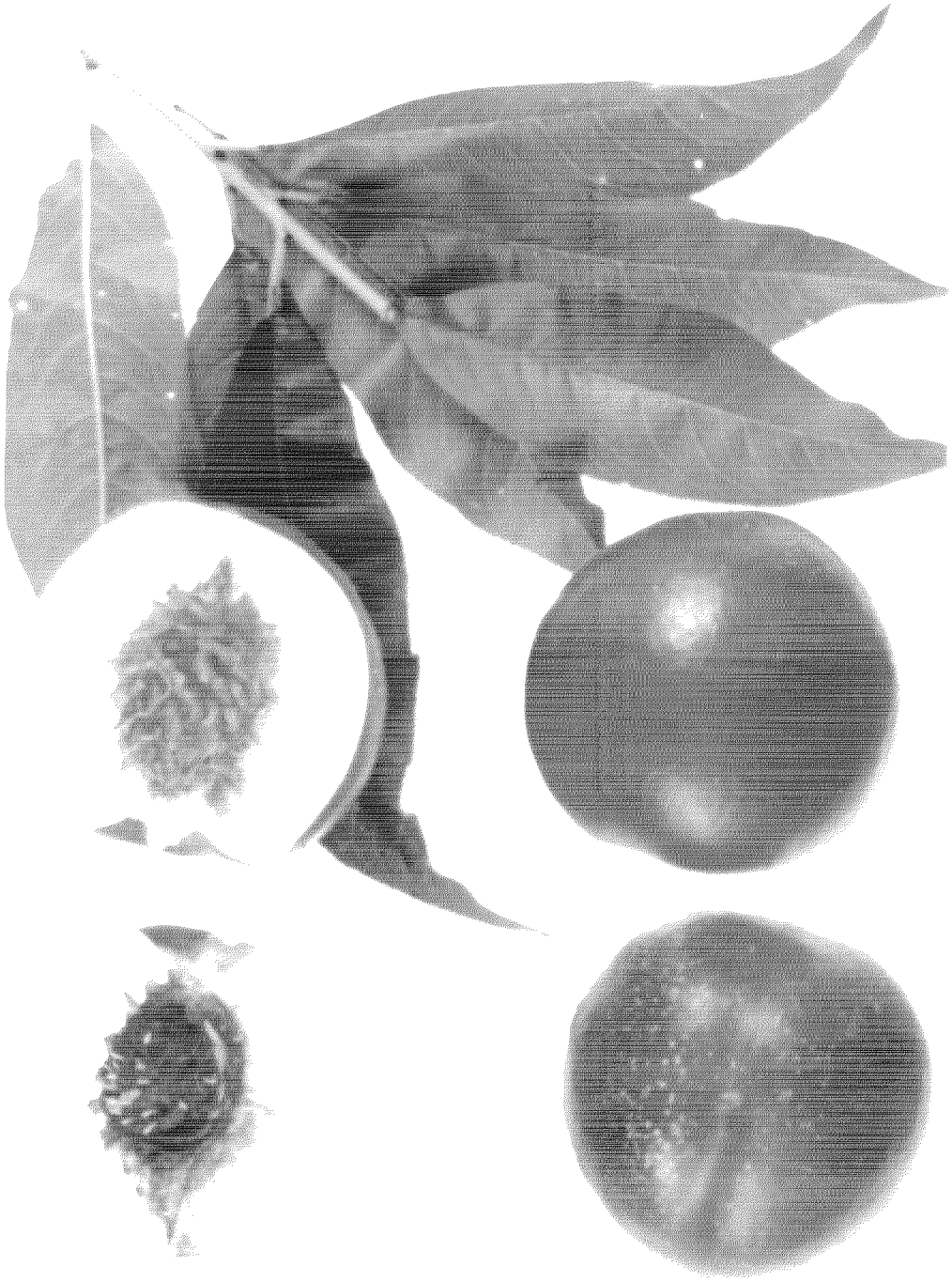

* * * * *